United States Patent [19]

Björk et al.

[11] Patent Number: 4,935,419
[45] Date of Patent: Jun. 19, 1990

[54] 1-PIPERAZINECARBOXAMIDE DERIVATIVES

[76] Inventors: Anders K. K. Björk, Svälvagen 9, S-230 50 Bjärred; Knut G. Olsson, Rörsjögatan 10, S-211 37 Malö; Aina L. Abramo, Järavallgatan 30, S-230 Bjärred; Erik G. Christensson, Nils Bjelkegatan 3a, S-222 20 Lund; Bengt K. R. Gustafsson, Svalvagen 36, S-237 00 Bjärred; Tomas Fex, Sporsnögatan 26, S-222 52 Lund, all of Sweden

[21] Appl. No.: 227,420
[22] Filed: Jul. 29, 1988

Related U.S. Application Data

[63] Continuation of Ser. No. 719,276, filed as PCT SE84/00269 on Aug. 2, 1983, published as WO85/00811 on Feb. 28, 1985, abandoned.

[30] Foreign Application Priority Data

Aug. 10, 1983 [SE] Sweden ............... 8304361

[51] Int. Cl.⁵ ............... A61K 31/495; C07D 241/04
[52] U.S. Cl. ............... 514/231.5; 514/255; 544/121; 544/386; 544/390; 544/391
[58] Field of Search ............... 544/386, 390, 391, 121; 514/255, 231.5

[56] References Cited

U.S. PATENT DOCUMENTS 3,000,892  9/1961  Janssen ............... 544/391
3,352,866  11/1967  Dornfield ............... 544/391

FOREIGN PATENT DOCUMENTS 2262521   9/1975  France ............... 544/391
2037745A  7/1980  United Kingdom ............... 544/391

OTHER PUBLICATIONS

Collection Czechoslov Chem. Commun., vol. 40, 1975, Rajsner et al., "1-[3-(4-Fluoroobenzoyl)propyl-]-4-Acylpiperazines and some Related Compounds", and Abstract.

Primary Examiner—Richard L. Raymond
Assistant Examiner—Raymond Covington
Attorney, Agent, or Firm—Browdy & Neimark

[57] ABSTRACT

A series of 1-piperazinecarboxamide derivatives of the following formula:

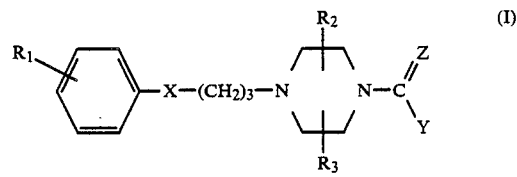

The compounds of the present invention are neuropharmacological agents intended for the treatment of mental disorders, such as psychoses and depression.

12 Claims, No Drawings 4,935,419

NOVEL 1-PIPERAZINECARBOXAMIDE DERIVATIVES

This application is a continuation of application Ser. No. 719,276, filed as PCT SE84/00269 on Aug. 10, 1983, published WO85/00811 on Feb. 28, 1985 now abandoned.

TECHNICAL FIELD

The present invention relates to novel compounds of the 1-piperazinecarboxamide type, methods for their preparation and therapeutical use. This invention is also related to pharmaceutical compositions containing the compounds. More particularly, the compounds are neuropharmacological agents intended for the treatment of mental disorders, such as psychoses and depression.

The object of the present invention is to provide compounds having a therapeutic activity in the central nervous system.

BACKGROUND OF THE INVENTION

There are known in the art a number of pharmacologicall active 1-piperazinecarboxamides which are substituted in the 4-position with an unsubstituted or substituted arylalkyl side chain or a functional derivative thereof. Such compounds may be found in the following references: Japan Kokai No. 76 08, 283 British Pat. No. 2,037,745.

There are also known in the art a number of butyrophenones derived from 1-acylpiperazine. They are reported to display a central depressant activity.

U.S. Pat. No. 3,000,892 describes as having central depressant and hypnotic activity compounds of formula

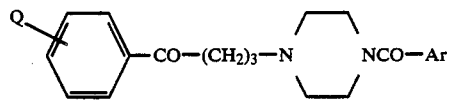

(A)

wherein Ar is a member of the class consisting of phenyl, methoxyphenyl, halophenyl, dimethoxyphenyl, and trimethoxyphenyl, and where Q is hydrogen, methoxy or halogen.

In the article "1-|3-(4-Fluorobenzoyl)propyl-|4-acyl-piperazines and some related compounds" by M. Rajsner et al. in Collect. Czech. Chem. Commun. 1975, 40(4), 1218–30, among the compounds described are those having the general formula

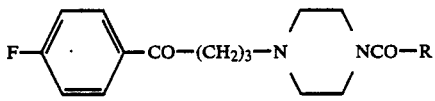

(B)

wherein R is OEt, Et, NH$_2$ and N(CH$_3$)$_2$. The compounds are reported to show only a slight central depressant activity which is apparent only in high doses.

Among the compounds disclosed by Swedish Pat. No. 350,497 are compounds under the general formula (B) wherein R is OR', where R' represents an alkyl group having from 1 to 4 carbon atoms, a cyclic hydrocarbon radical, e.g. cyclohexyl or an arylalkyl group, e.g. benzyl. The compounds have for example neuroleptic properties.

The compounds of the present invention differ from the foregoing essentially by being 1-piperazinecarboxamides, having particular substituent groups in the 4-position, or by having a special combination of substituent groups in the 4-position and on the nitrogen in the amide function.

The pharmacological properties which clearly distinguish the compounds of the present invention from what is known in the art are described under the heading "Pharmacological Properties".

DESCRIPTION OF THE INVENTION

This invention is concerned with a novel series of 1-piperazinecarboxamide derivatives which are structurally represented by formula (I),

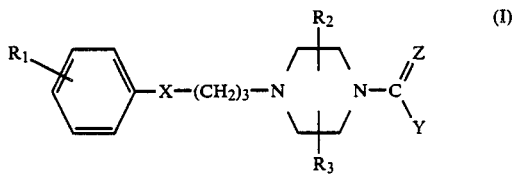

(I)

and the pharmaceutically acceptable acid addition salts thereof;

wherein R$_1$ is a member selected from hydrogen, halogen or trifluoromethyl;

wherein X is selected from:

≧CO (Ia)

≧CHOH (Ib) ≧CHOR$_8$ (Ib') ≧CHOCOR$_8$ (Ib")

≧CH$_2$ (Ic)

≧C=CR$_6$R$_7$ (Id)

≧CH—CHR$_6$R$_7$ (Ie)

(If)

wherein R$_2$ and R$_3$ are the same or different and selected from hydrogen or lower alkyl;

wherein Z is either oxygen or sulfur;

wherein Y is —NR$_4$R$_5$, where R$_4$ and R$_5$ are the same or different and selected from hydrogen, alkyl, alkenyl, cycloalkyl, aryl, aryl-(lower alkyl), or R$_4$ and R$_5$ may together with the N-atom form a 5- or 6- or 7-membered saturated ring, where one of the carbon atoms may be exchanged for O, NR$_8$ or NCOR$_8$;

wherein R$_6$ and R$_7$ are the same or different and selected from hydrogen or lower alkyl;

wherein R$_8$ is lower alkyl or lower alkenyl;

and when used in the foregoing definitions the term "lower alkyl" is meant to include straight and branched hydrocarbon radicals having from 1 to 4 carbon atoms; the term "lower alkenyl" is meant to include straight and branched alkenyl radicals having from 2 to 4 carbon atoms; the term "alkyl" is meant to include straight and branched hydrocarbon radicals having from 1 to 10 carbon atoms; the term "alkenyl" is meant to include straight and branched alkenyl radicals having from 2 to 10 carbon atoms; the term "cycloalkyl" is meant to include cyclic hydrocarbon radicals having from 3 to 8 carbon atoms; the term "aryl" is meant to include phenyl and substituted phenyl, wherein said substituted phenyl has from 1 to 3 substituents, each independently selected from the group consisting of halogen, methyl, methoxy, trifluoromethyl and NR$_2$R$_3$; and the term "halogen" is generic to include fluoro, chloro and bromo;

with the provisio that when X is CO, then $R_4$ is hydrogen and $R_5$ is different from hydrogen.

Among the compounds covered by the general formula (I), it is preferred that $R_1$ is halogen or $CF_3$ and that said substituent is situated in m- or p-positions.

If selected from halogen atoms it is preferred that $R_1$ is F or Cl, especially F.

When $R_1$ is $CF_3$ it is preferably situated in the m-position.

It is preferred that $R_2$ and $R_3$ are hydrogen.

When $R_2$ and $R_3$ are lower alkyl groups, methyl and ethyl are preferred, especially methyl.

One group of preferred compounds are those where X is $CH_2$, $C=CR_6R_7$ or $CHCHR_6R_7$.

When X is selected from the groups CHOH, $CHOR_8$ and $CHOCOR_8$, compounds are preferred wherein X is $CHOR_8$ or $CHOCOR_8$, especially $CHOR_8$.

Preferred compounds are also those wherein X is CO.

For compounds where the group X have polar properties (such as when X is CO or CHOH), higher water solubility is to be anticipated.

Compounds where the substituent X have nonpolar properties (such as when X is $CH_2$, $C=CR_6R_7$, $CHCHR_6R_7$, $CHOR_8$ or $CHOCOR_8$) will show a greater tendency to participate in hydrophobic interactions. The non-polar properties increase with increasing chain length of substituents $R_6$, $R_7$ and $R_8$.

Compounds wherein Z is S are markedly more non-polar than those where Z is O. Thus, compounds of general formula (I) where Z is S are of particular interest when other groups or substituents are of polar nature, such as when X is CO or CHOH.

As regards to substituents $R_6$ and $R_7$, those compounds are preferred wherein one of said substituents is hydrogen or methyl.

As regards to substituents $R_4$ and $R_5$, those compounds are preferred wherein $R_4$ is hydrogen and $R_5$ is alkyl or alkenyl or wherein $R_4$ and $R_5$ together with the N-atom form a ring, and especially preferred are those wherein $R_4$ and $R_5$ together contain less than nine carbon atoms.

When $R_4$ and $R_5$ together with the N-atom form a ring which contain an additional heteroatom (N or O), then a 6-membered ring is preferred, and those compounds are preferred where the additional heteroatom is O.

The compounds of formula (I) have basic properties and consequently they may be converted to their therapeutically active nontoxic acid addition salts by treatment with appropriate acids; e.g. inorganic acids such as hydrochloric, hydrobromic, sulfuric, nitric and phosphoric acid, or organic acids such as acetic, propanoic, glycolic, lactic, malonic, succinic, fumaric, tartaric, citric and pamoic acid.

Conversely, the salt form can be converted into the free base form by treatment with alkali.

METHODS OF PREPARATION

Compounds of formula (Ia, b, b', b'', c, d, e, f) may be prepared according to Methods 1 and 2. Compounds of formula (Ia, c, d, e, f) may be prepared according to Method 3. Compounds of formula (Ia, b, b', b'', c, d, e) where $R_4$ and $R_5$ are both hydrogen, may be prepared according to Method 4. Compounds of formula (Ia) may be prepared according to Method 5. Compounds of formula (Ib) may be prepared according to Method 6. Compounds of formula (Ib') may be prepared according to Method 7. Compounds of formula (Ib'') may be prepared according to Method 8. Compounds of formula (Ic, e) may be prepared according to Method 9. Compounds of formula (Ib', c, d, e, f) may be prepared according to Method 10. Methods 11, 12, 13, 14, 15 and 16 describes procedures for preparation of intermediates.

Method 1

Compounds of formula (Ia, b, b', b'', c, d, e, f) can be prepared by reaction of compounds of formula (II) ($R_1$, X, $R_2$, $R_3$ are as defined above) with an isocyanate of formula (III), or an isothiocyanate of formula (IV), or a carbamoyl chloride of formula (V), or a compound of formula (VI).

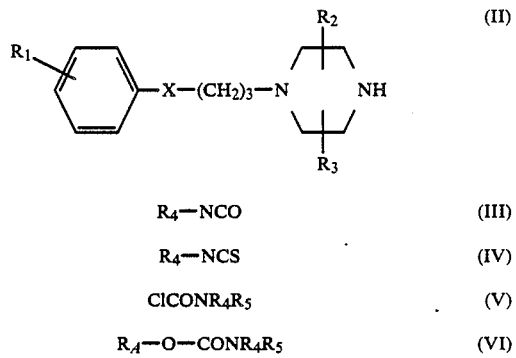

$R_4$ and $R_5$ are as defined above. $R_A$ represents a phenyl group or when neither of the substituents on the N-atom is hydrogen, preferably a substituted phenyl group (preferably electronegative substituents, especially p-nitro).

The reactions may be carried out using standard procedures, and are thus preferably performed in organic solvents such as diethyl ether, chloroform, toluene and the like. The mixtures are reacted over a wide range of temperatures, from about 0° C. to about 110° C., although it is possible to employ temperatures above and below this range. The reactions may be carried out in the presence of a base, e.g. triethylamine or potassium carbonate.

Method 2

Compounds of formula (Ia, b, b', b'', c, d, e, f) may be prepared by reacting appropriate compounds of formula (VII) ($R_1$, X, $R_2$, $R_3$ and RA are as defined above) with the appropriate amine ($R_4$ and $R_5$ are as defined above).

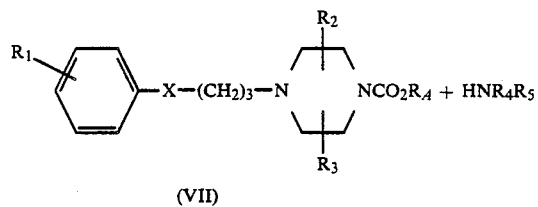

The reaction is performed using a large excess of the amine as solvent, or a smaller excess is combined with a suitable co-solvent, such as; the lower alkanols (e.g. methanol, ethanol, propanol, butanol) or an aromatic hydrocarbon (e.g. benzene, toluene, xylene). Heating may be used to facilitate the reaction, and is required when less reactive amines are used.

Method 3

Compounds of formula (Ia, c, d, e, f) can be prepared by reaction of an appropriate compound (VIII) ($R_1$ and X are as previously defined and W is a suitable leaving group such as halogen or alkyl- or aryl-sulfonate) with a compound of formula (IX) ($R_2$, $R_3$, Z and Y are as defined above).

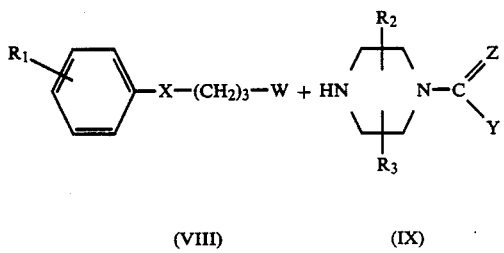

(VIII)    (IX)

The reaction may be carried out using standard N-alkylating procedures. It is thus preferably performed in an inert solvent such as a lower alkanol (e.g. methanol, ethanol, propanol, butanol) or an aromatic hydrocarbon (e.g. benzene, toluene, xylene). The addition of an appropriate base such as an amine (e.g. triethylamine), or an alkali or earth alkaline metal carbonate or hydrogen carbonate may be useful in order to neutralize the acid which is liberated during the reaction. A small amount of a metal iodide (e.g. sodium or potassium iodide) may be added as a reaction promotor. Somewhat elevated temperatures may be required to enhance the rate of reaction, and in several cases the reaction is preferably performed at the reflux temperature of the reaction mixture.

Method 4

Compounds of formula (Ia, b, b', b'', c, d, e), where $R_4$ and $R_5$ are both hydrogen, may be prepared by reaction of compounds of formula (II) with an appropriate cyanate or thiocyanate (e.g. an alkali metal cyanate or alkali metal thiocyanate) in acidic media (e.g. acetic acid or a mixture of acetic acid and water). Heating may be required.

Method 5

Compounds of formula (Ia) may be prepared from compounds of formula (If) using a mild acid hydrolysis according to standard procedures. It may thus be performed in a suitable solvent such as a mixture of a lower alkanol (e.g. methanol, ethanol and the like) and water, to which a suitable acid (e.g. hydrochloric) has been added. Heating facilitates the reaction.

Method 6

Compounds of formula (Ib) can be prepared by reduction of a compound of formula (Ia) with an appropriate reducing agent, e.g. sodium borohydride and the like. The reduction is carried out following standard procedures. A compound of formula (Ia) is thus stirred in a suitable solvent (e.g. ethanol and the like) in the presence of the reducing agent (e.g. sodium borohydride and the like). External cooling may be required.

Method 7

Compounds of formula (Ib') (where neither of $R_4$ or $R_5$ is hydrogen) may be prepared by reacting an appropriate compound of formula (Ib) with a compound of formula $R_8$-W ($R_8$ and W are as defined above) under strongly basic conditions. Thus the reaction is performed in an inert apolar solvent such as ether, tetrahydrofuran, toluene or the like, or in an inert polar solvent such as DMF, DMSO or the like, using a strong base such as sodium or potassium hydride as the base. The reaction may be performed at a wide range of temperatures and less reactive compounds of formula $R_8$-W may require refluxing of the reaction mixture.

Method 8

Compounds of formula (Ib'') may be prepared by reacting an appropriate compound of formula (Ib) with a suitable acylating agent such as an acid halide or acid anhydride. The reaction is preferably performed in the presence of a base (e.g. pyridine, triethylamine) in an inert solvent (e.g. ether, toluene), or the base may be utilized as solvent (e.g. pyridine).

Method 9

Compounds of formula (Ie) may be prepared via hydrogenation of compounds of formula (Id) using standard hydrogenating procedures. The reaction may thus be performed in a suitable solvent such as the lower alkanols (e.g. methanol, ethanol, propanol, butanol), ethyl acetate, tetrahydrofuran or dioxane, in the presence of hydrogen and a suitable noble metal catalyst. The use of acidic reaction media, such as acetic acid, may enhance the reaction rate.

Compounds of formula (Ic) may be prepared from compounds of formula (Ia, b, b', b'', f) using similar hydrogenationg procedures.

Method 10

Compounds of formula (Ib', c, d, e, f) wherein both $R_4$ and $R_5$ are different from hydrogen and wherein Z is O may be prepared from compounds of formula (Ib', c, d, e, f) wherein one of $R_4$ or $R_5$ is hydrogen and Z is O via alkylation using an alkylating agent $R_8$—W (defined above) and using alkylating conditions similar to those described in Method 7.

Method 11

Compounds of formula (IIa, c, d, e, f) may be prepared by reaction of the appropriate compound of formula (VIII) ($R_1$, X and W are as defined above) with a large excess of a piperazine ($R_2$ and $R_3$ are as defined above).

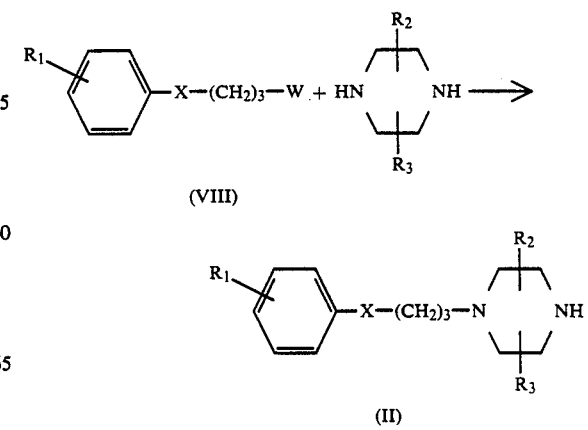

(VIII)

(II)

The reaction is carried out using standard N-alkylating procedures as described in Method 3.

Method 12

Compounds of formula (IIa, c, d, e) may be prepared by the following reaction sequence:

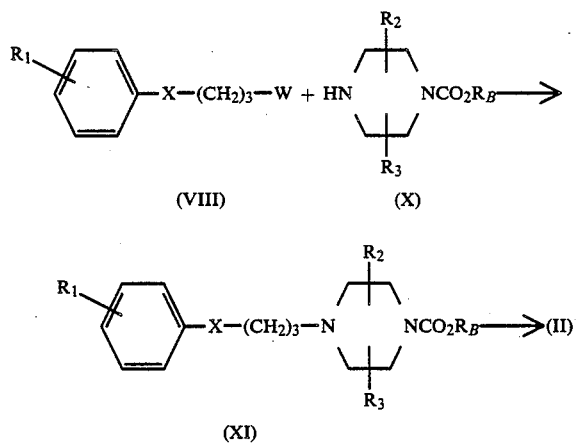

$R_1$, X, W, $R_2$ and $R_3$ are as defined above. $R_B$ is lower alkyl (e.g. methyl, ethyl, isobutyl).

The N-alkylation of (VIII) to form (XI) is performed according to standard procedures described in Method 3.

The hydrolysis of (XI) to form (II) is performed according to standard procedures. Thus it may conveniently be carried out by stirring and heating, preferably refluxing, compounds of formula (XI) and an alkali hydroxide (e.g. potassium hydroxide and the like) in a suitable solvent such as a lower alkanol (e.g. methanol, ethanol, propanol, butanol). Alternatively the hydrolysis may be carried out using acidic conditions such as HBr in acetic acid.

Method 13

Compounds of formula (IIb') may be prepared by reacting a compound of formula (IIb) with an appropriate alkylating agent $R_8$—W ($R_8$ and W are as defined above) using similar reaction conditions to these described under Method 7.

Method 14

Compounds of formula (IId) may be prepared from compounds of formula (IIa) via a Wittig reaction, using the appropriate Wittig reagent (XII) ($R_6$ and $R_7$ are as defined above) and using standard procedures.

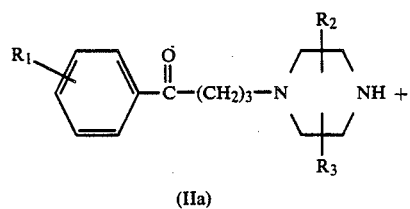

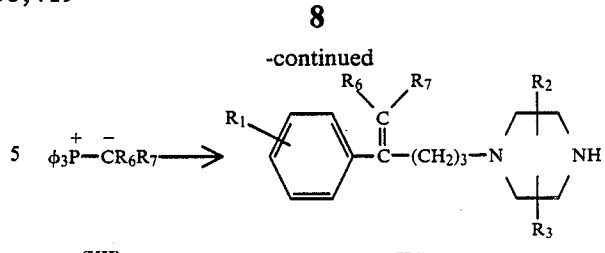

The reaction is carried out in an inert solvent such as tetrahydrofuran or ether, preferably tetrahydrofuran. Heating facilitates the reaction, and refluxing the reaction mixture may be required in some instances.

Method 15

Compounds of formula (IIe) may be prepared via hydrogenation of compounds of formula (IId) using standard procedures as described in Method 9.

Method 16

Compounds of formula (VII) may be prepared by reacting compounds of formula (II) with the appropriate chlorocarbamate $ClCO_2R_A$ ($R_A$ is as defined above). The reaction is carried out under standard acylating conditions. Thus the reaction is performed in an inert solvent such as ether, chloroform or toluene. The reaction mixture is generally cooled, and a base e.g. triethylamine is added to take care of the acid formed during the reaction.

The reaction can alternatively be carried out using a two phase mixture containing the organic solvent mentioned above and a waterphase containing an appropriate base e.g. magnesium oxide.

EXAMPLES

The following examples are intended to illustrate but not to limit the scope of the invention, although the compounds named are of particular interest for our intended purposes. These compounds have been designated by a number code, a:b, where a means the number of the example wherein the preparation of the compound in question is described, and b refers to the order of the compounds prepared according to that example. Thus, compound 1:2 means the second compound prepared according to Example 1.

The structures of the compounds are confirmed by NMR, mass spectra and elementary analysis. When melting points are given, these are uncorrected.

EXAMPLE 1

4-|4-(p-fluorophenyl)butyl|-N-methyl-1-piperazinecarboxamide hydrochloride

To a stirred solution of 0.97 g (0.017 mole) of methyl isocyanate in 35 ml of toluene was added dropwise over a period of 20 minutes at 5° C. 4.0 g (0.017 mole) of 1-|4-(p-fluorophenyl)butyl|piperazine in 20 ml of toluene. The mixture was then stirred at 30°–40° C. for 2 hours and evaporated to yield the free base of the title compound. This was dissolved in ethanol-ether and acidified with ethanolic HCl. The solid, which precipitated, was collected by filtration and recrystallized from 2-propanol yielding 4.0 g of 4-|4-(p-fluorophenyl)-butyl|-N-methyl-1-piperazinecarboxamide hydrochloride (1:1); mp 195°–97° C. Using essentially the same procedure the following compounds are prepared (isolated as free bases or as the corresponding salts) from the corresponding starting materials:

1:2  4-|4-(p-fluorophenyl)-4-oxobutyl|-N-methyl-1-piperazinecarboxamide hydrochloride mp 185°-6° C.

1:3  4-|4-(p-fluorophenyl)-4-oxobutyl|-N-ethyl-1-piperazinecarboxamide hydrochloride mp 190°-1° C.

1:4  4-|4-(p-fluorophenyl)-4-oxobutyl|-N-(1-methylethyl)-1-piperazinecarboxamide hydrochloride mp 217°-18° C.

1:5  4-|4-(p-fluorophenyl)-4-oxobutyl|-N-propyl-1-piperazinecarboxamide hydrochloride mp 207°-9° C.

1:6  4-|4-(p-fluorophenyl)-4-oxobutyl|-N-(1,1-dimethylethyl)-1-piperazinecarboxamide 1:7  4-|4-(p-fluorophenyl)-4-oxobutyl|-N-cyclohexyl-1-piperazinecarboxamide hydrochloride mp 230° C. (dec)

1:8  4-|4-(p-fluorophenyl)-4-oxobutyl|-N-(p-methoxyphenyl)-1-piperazinecarboxamide 1:9  4-|4-(p-chlorophenyl)-4-oxobutyl|-N-ethyl-1-piperazinecarboxamide 1:10  4-(4-oxo-4-phenylbutyl)-N-ethyl-1-piperazinecarboxamide 1:11  4-|4-(m-trifluoromethylphenyl)-4-oxobutyl|-N-ethyl-1-piperazinecarboxamide 1:12  4-|4-(p-bromophenyl)-4-oxobutyl|-N-ethyl-1-piperazinecarboxamide 1:13  4-|4-(p-fluorophenyl)-4-oxobutyl|-2,5-trans-dimethyl-N-ethyl-1-piperazinecarboxamide oxalate mp 160° C.

1:14  4-|4-(p-fluorophenyl)-4-oxobutyl|-3,5-(cis-dimethyl-N-ethyl-1-piperazinecarboxamide hydrochloride mp 146°-8° C.

1:15  4-|4-(p-fluorophenyl)butyl|-N-ethyl-1-piperazinecarboxamide hydrochloride mp 193°-5° C.

1:16  4-|4-(p-fluorophenyl)butyl|-N-(1-methylethyl)-1-piperazinecarboxamide hydrochloride mp 208°-9° C.

1:17  4-|4-(p-fluorophenyl)butyl|-N-(1,1-dimethylethyl)-1-piperazinecarboxamide

1:18  4-|4-(p-fluorophenyl)butyl|-N-cyclohexyl-1-piperazinecarboxamide hydrochloride mp 252°-4° C.

1:19  4-|4-(p-fluorophenyl)butyl|-N-phenyl-1-piperazinecarboxamide hydrochloride mp 245°-7° C.

1:20  4-|4-(p-fluorophenyl)butyl|-N-benzyl-1-piperazinecarboxamide hydrochloride mp 189°-90° C.

1:21  4-|4-(p-fluorophenyl)butyl|-N-(m-trifluoromethylphenyl)-1-piperazinecarboxamide hydrochloride mp 190°-1° C.

1:22  4-|4-(p-fluorophenyl)butyl|-N-(p-methoxyphenyl)-1-piperazinecarboxamide hydrochloride mp 235° C. (dec)

1:23  4-(4-phenylbutyl)-N-ethyl-1-piperazinecarboxamide hydrochloride mp 201°-3° C.

1:24  4-|4-(p-chlorophenyl)butyl|-N-ethyl-1-piperazinecarboxamide

1:25  4-|4-(m-trifluoromethylphenyl)butyl|-N-ethyl-1-piperazinecarboxamide

1:26  4-|4-(p-bromophenyl)butyl|-N-ethyl-1-piperazinecarboxamide

1:27  4-|4-(p-fluorophenyl)butyl|-2,5-trans-dimethyl-N-methyl-1-piperazinecarboxamide oxalate mp 186°-7° C. (dec)

1:28  4-|4-(p-fluorophenyl)butyl|-2,5-trans-dimethyl-N-ethyl-1-piperazinecarboxamide 1 1|2 fumarate mp 99°-102° C.

1:29  4-|4-(p-fluorophenyl)butyl|-3,5-cis-dimethyl-N-ethyl-1-piperazinecarboxamide hydrochloride mp 200°-1° C.

1:30  4-|4-(p-fluorophenyl)-4-pentenyl|-N-ethyl-1-piperazinecarboxamide hydrochloride mp 195°-6° C.

1:31  4-|4-(p-fluorophenyl)-4-pentenyl|-N-cyclohexyl-1-piperazinecarboxamide

1:32  4-(4-phenyl-4-pentenyl)-N-ethyl-1-piperazinecarboxamide

1:33  4-|4-(p-chlorophenyl)-4-pentenyl|-N-ethyl-1-piperazinecarboxamide

1:34  4-|4-(m-trifluoromethylphenyl)-4-pentenyl|-N-ethyl-1-piperazinecarboxamide 1:35  4-|4-(p-fluorophenyl)-4-pentenyl|-2,5-trans-dimethyl-N-ethyl-1-piperazinecarboxamide 1:36  4-|4-(p-fluorophenyl)-5-methyl-4-hexenyl|-N-ethyl-1-piperazinecarboxamide hydrochloride 1:37  4-|4-(p-fluorophenyl)-4-octenyl|-N-ethyl-1-piperazinecarboxamide oxalate mp 174° C.

1:38  4-|4-(p-fluorophenyl)pentyl|-N-ethyl-1-piperazinecarboxamide hydrochloride mp 190°-1° C.

1:39  4-|4-(p-fluorophenyl)-5-methylhexyl|-N-ethyl-1-piperazinecarboxamide hydrochloride mp 176°-7° C.

1:40  4-|4-(p-fluorophenyl)octyl|-N-ethyl-1-piperazinecarboxamide oxalate mp 150° C.

1:41  4-|4-(p-chlorophenyl)pentyl|-N-ethyl-1-piperazinecarboxamide

1:43  4-(4-phenylpentyl)-N-ethyl-1-piperazinecarboxamide

1:44  4-|4-(p-fluorophenyl)-4-ethoxybutyl|-N-ethyl-1-piperazinecarboxamide

1:45  4-|4-(p-fluorophenyl)-4,4-ethylenedioxy-butyl|-N-ethyl-1-piperazinecarboxamide 1:46  4-|4-(p-fluorophenyl)butyl|-2,5-cis-dimethyl-N-ethyl-1-piperazinecarboxamide

EXAMPLE 2

4-|4-(p-fluorophenyl)butyl|-N-methyl-piperazinethiocarboxamide hydrochloride 5.0 g (0.02 mole) of 1-|4-(p-fluorophenyl)butyl|piperazine was dissolved in 50 ml of ether. 1.55 g (0.02 mole) of methylisothiocyanate in 10 ml ether was added dropwise at room temperature. The mixture was stirred for 3 hours at room temperature whereby the free base of the title compound crystallized. It was filtered off, dissolved in ethanol, and HCl in ethanol added to form the hydrochloride. Ether was added to precipitate the hydrochloride, and it was filtered off. Recrystallization from 2-propanol yielded 4.5 g of the title compound, (2:1) mp 151°-2° C.

Using essentially the same procedure the following compounds are prepared (isolated as the free bases or as the corresponding salts) from the corresponding starting materials.

2:2  4-|4-(p-fluorophenyl)-4-oxobutyl|-N-methyl-1-piperazinethiocarboxamide hydrochloride mp 176°-7° C.

2:3  4-|4-(p-fluorophenyl)-4-pentenyl|-N-methyl-1-piperazinethiocarboxamide

EXAMPLE 3

4-(4-phenylbutyl)-N-ethyl-1-piperazinecarboxamide hydrochloride

A mixture of 4.4 g (0.02 mole) of 1-phenylbutyl-piperazine, 3.3 g (0.02 mole) of phenyl-N-ethyl-carbamate, and 4.0 g of $K_2CO_3$ in 60 ml toluene was refluxed for 1 hour. After cooling and filtration the solvents were evaporated. The residue was dissolved in ether and HCl in EtOH was added. The hydrochloride thus formed was filtered off and subsequently dissolved in water.

After one extraction with ether the water solution was made alkaline with NaOH and the oil which formed was extracted into ether. The ether phase was washed with sat. NaCl-solution, dried over $Na_2SO_4$ and evaporated to yield the free base of the title compound. This was dissolved in ether and HCl in EtOH was added to precipitate the hydrochloride, and this was filtered off. Recrystallization from EtOH/EtOAc acetat yielded 3.5 g of the title compound; (3:1) mp 201°–3° C. (3:1 is the same as 1:23) Using essentially the same procedure the following compounds are prepared (isolated as the free bases or as the corresponding salts) from the corresponding starting materials.

3:2 4-|4-(p-fluorophenyl)-4-oxobutyl|-N-cyclopropyl-1-piperazinecarboxamide hydrochloride mp 211°–12° C.

3:3 4-|4-(p-fluorophenyl)-4-oxobutyl|-N-butyl-1-piperazinecarboxamide

3:4 4-|4-(p-fluorophenyl)-4-oxobutyl|-N-pentyl-1-piperazinecarboxamide

3:5 4-|4-(p-fluorophenyl)-4-oxobutyl|-N-hexyl-1-piperazinecarboxamide

3:6 4-|4-(p-fluorophenyl)-4-oxobutyl|-N-(p-chlorophenyl)-1-piperazinecarboxamide 3:7 4-|4-(p-fluorophenyl)butyl|-N-cyclopropyl-1-piperazinecarboxamide hydrochloride mp 214°–16° C.

3:8 4-|4-(p-fluorophenyl)butyl|-N-pentyl-1-piperazinecarboxamide hydrochloride mp 202°–4° C.

3:9 4-|4-(p-fluorophenyl)butyl|-N-octyl-1-piperazinecarboxamide hydrochloride mp 215°–16° C.

3:10 4-|4-(p-fluorophenyl)butyl|-N-(2-phenylethyl)-1-piperazinecarboxamide hydrochloride mp 193°–4° C.

3:11 4-|4-(p-fluorophenyl)butyl|-N-(p-chlorophenyl)-1-piperazinecarboxamide hydrochloride mp 229°–30° C.

EXAMPLE 4

1-pyrrolidinocarbonyl-4-4-(p-fluorophenyl)butyl|piperazine hydrochloride 3.5 g (8.7 mmole) of 4-|4-(p-fluorophenyl)butyl|-1-carbo-(p-nitrophenoxy)|piperazine was dissolved in 20 ml of pyrrolidine, and left at room temperature for 1 hour. The reaction mixture was partitioned between 100 ml of $H_2O$ and of 100 ml of ether containing some ligroin. The organic phase was separated and washed 3 times with sat. NaCl solution. Drying and evaporation of the solvents yielded the free base of the title compound. This was dissolved in EtOAc, and the hydrochloride precipitated with HCl in EtOH. Recrystallization from EtOAc|EtOH yielded 2.3 g of the title compound; (4:1) mp 213°–15° C.

Using essentially the same procedure the following compounds are prepared (isolated as free bases or as the corresponding salts) from the corresponding starting materials.

4:2 4-|4-(p-fluorophenyl)butyl|-N,N-dimethyl-1-piperazinecarboxamide hydrochloride mp 165° C.

4:3 4-|4-(p-fluorophenyl)butyl|-N,N-diethyl-1-piperazinecarboxamide hydrochloride mp 200°–2° C.

4:4 1-morpholinocarbonyl-4-|4-(p-fluorophenyl|butyl-piperazine hydrochloride mp 186°–7° C.

4:5 1-(4-methylpiperazinocarbonyl)-4-|4-(p-fluorophenyl)butyl|piperazine

4:6 1-(4-acetylpiperazinocarbonyl)-4-|4-(p-fluorophenyl)butyl|piperazine

4:7 4-|4-(p-fluorophenyl)-4-pentenyl|-N,N-dimethyl-1-piperazinecarboxamide

4:8 1-pyrrolidinocarbonyl-4-|4-(p-fluorophenyl)-4-pentenyl|piperazine

4:9 1-morpholinocarbonyl-4-|4-(p-fluorophenyl)-pentyl|piperazine

EXAMPLE 5

4-|4-(p-fluorophenyl)butyl|-1-piperazinecarboxamide 3.5 g (0.015 mole) of 1-|4-(p-fluorophenyl)butyl|piperazine was dissolved in 25 ml of acetic acid containing 10% water. 1.6 g of potassium cyanate in 10 ml of water was added at room temperature during 15 minutes. The mixture was stirred for 15 hours. 50 ml of water was added, the mixture cooled to 0° C. and 80 ml of 5N NaOH was slowly added. After stirring for 4 hours the crystalline product was filtered off, and washed with water. The solid was dissolved in $CH_2Cl_2$, and the organic phase washed with water. After drying with $Na_2SO_4$ the solvents were evaporated. The residue was recrystallized from toluene/ligroin to yield 3.3 g of the title compound (5:1); mp 82°–84° C.

The corresponding hydrochloride has mp 220°–1° C. (5:2)

Using essentially the same procedures the following compound is prepared (isolated as the free base) from the corresponding starting materials.

5:3 4-|4-(p-fluorophenyl)butyl|-1-piperazinethiocarboxamide

EXAMPLE 6

4-|4-(p-fluorophenyl)-4-oxobutyl|-N-ethyl-1-piperazinecarboxamide hydrochloride

To a solution of 14.7 g of crude 4-|4-(p-fluorophenyl)-4,4-ethylenedioxy-butyl|-N-ethyl-1-piperazinecarboxamide in 25 ml of ethanol was added 25 ml of 5N ethanolic HCl. The mixture was refluxed 15 minutes. After cooling 250 ml of ether was added. The solid, which precipitated, was recrystallized from ethanol giving 7,0 g of 4-|4-(p-fluorophenyl)-4-oxobutyl|-N-ethyl-1-piperazinecarboxamide hydrochloride; (6:1) mp 190°–91° C. (6:1 is the same as 1:3)

EXAMPLE 7

4-|4-(p-fluorophenyl)-4-hydroxybutyl|-N-ethyl-1-piperazinecarboxamide hydrochloride To a stirred slurry of 0.9 g of sodium borohydride in 30 ml of ethanol was added dropwise 3.9 g (0.012 mole) of 4-|4-(p-fluorophenyl)-4-oxobutyl|-N-ethyl-1-piperazinecarboxamide in 30 ml of ethanol. The reaction mixture was stirred at room temperature 4 hours. Then dilute HCl was added slowly and when hydrogen no longer was evolved the mixture was concentrated. The oily residue was dissolved in $H_2O$ and extracted with ether (which was discarded). The aqueous phase was made basic with NaOH solution and extracted with $CH_2Cl_2$. The organic phase was dried and evaporated to yield the free base of the title compound. This was dissolved in ethanol and acidified with ethanolic HCl. Ether was added. The solid, which precipitated, was collected by filtration and recrystallized from 2-propanol giving 3.1 g of 4-|4-(p-fluorophenyl)-4-hydroxybutyl|-N-ethyl-1-piperazinecarboxamide hydrochloride (7:1); mp 167°–68° C.

The free base was acylated using propionic anhydride in pyridine to yield 4-|4-(p-fluorophenyl)-4-propionyloxybutyl|-N-ethyl-1-piperazinecarboxamide (7:2).

Using essentially the same procedure the following compounds are prepared (isolated as the free base or as the corresponding salt) from the corresponding starting materials.

7:3   4-|4-(m-trifluoromethylphenyl)-4-hydroxybutyl|-N-ethyl-1-piperazinecarboxamide
7:4   4-|4-(p-fluorophenyl)-4-hydroxybutyl|-N-methyl-1-piperazinethiocarboxamide

EXAMPLE 8

4-|4-(p-fluorophenyl|butylpiperazine

A solution of 18.7 g (0.1 mole) of 1-chloro-4-(p-fluorophenyl)butane and 60.3 g of (0.7 mole) piperazine in 250 ml of isopropanol was refluxed for 24 hours. The solvent was evaporated. Water was added to the residue, and extracted several times with ether. The combined ether extracts were washed with sat. NaCl-solution, and dried over anhydrous $K_2CO_3$. The ether was evaporated, and the residue distilled to yield 18.9 g of the title compound; bp 96°–100° C. (0.02 mm Hg).

EXAMPLE 9

1-carboethoxy-4-|4-(p-fluorophenyl)butyl|piperazine hydrochloride

To a solution of 20.2 g (0.11 mole) of 1-chloro-4-(p-fluorophenyl)butane in 110 ml of n-butanol was added 18.0 g (0.11 mole) of 1-carboethoxypiperazine, 17.2 g of sodium carbonate and 0.1 g of potassium iodide. The mixture was stirred and heated at reflux for 24 hours. The reaction mixture was filtered and the solvent was removed. The residue was dissolved in ether, washed with NaCl solution, dried over $Na_2SO_4$ and distilled to give 29,7 g of 1-carboethoxy-4-|4-(p-fluorophenyl)-butyl|piperazine; bp 137°–42° C. (0.05 mm). The hydrochloride has mp 154°–5° C.

EXAMPLE 10

1-|4-(p-fluorophenyl)butyl|piperazine

To a solution of 19.8 g of potassium hydroxide in 200 ml of 2-propanol was added 30.8 g (0.10 mole) of 1-carboethoxy-4-|4-(pfluorophenyl)butyl|piperazine. The mixture was stirred and refluxed 26 hours. The reaction mixture was cooled, filtered and concentrated. The oily residue was treated with ether. The mixture was filtered and distilled to give 17.2 g of 1-|4-(p-fluorophenyl)-butyl|piperazine; bp 112°–17° C. (0.1 mm).

EXAMPLE 11

4-|4-(p-fluorophenyl)butyl|-1-|carbo-(p-nitrophenoxy)|-piperazine 18.0 g (0.076 mole) of 1-|4-(p-fluorophenyl)butyl| piperazine was dissolved in 200 ml of ether +50 ml of EtOAc. 150 ml of $H_2O + 18$ g of MgO were added and the mixture stirred vigorously at 0° C. 16.0 g (0.08 mole) of p-nitrophenylchloroformate in 100 ml of ether was added during 0.5 hour. The reaction product crystallized in the mixture, and to dissolve it EtOAc and some EtOH were added. The organic layer was separated and washed with 1N NaOH and 3 times with sat. NaCl-solution. After drying and evaporation of the solvents the residue was taken up in EtOAc/ligroin, and a total of 19.2 g of the title compound crystallized: mp 85°–86° C. The hydrochloride has mp 207°–8° C.

EXAMPLE 12

1-|4-(p-fluorophenyl)-4-pentenyl|piperazine 20.0 g of "instant ylid" (a 1:1 mixture of methyl-triphenylphosphonium bromide and sodium amide) was dissolved in 100 ml of tetrahydrofuran and stirred for 10 minutes at room temperature. 10.5 g (0.042 mole) of 1-|4-(p-fluorophenyl)-4-oxobutylpiperazine dissolved in 20 ml of tetrahydrofuran was added during 10 min. The reaction mixture was stirred over-night at room temperature. 100 ml of ether was added and subsequently also ligroin in order to precipitate the triphenylphosphine formed during the reaction. The solid material was filtered off, and the solvents evaporated under vacuum. The residue was distilled to give 5.5 g of the title compound; bp 103°–6° C. (0.08 mm Hg).

EXAMPLE 13

4-|4-(p-fluorophenyl)pentyl|-N-ethyl-1-piperazinecarboxamide hydrochloride 4.6 g (13 mmole) of 4-|4-(p-fluorophenyl)-4-penteny|N-ethyl-1-piperazinecarboxamide hydrochloride was dissolved in 125 ml of abs. ethanol and 0.5 g of 5% palladium on carbon was added. The mixture was hydrogenated at 40 psi at room temperature. The catalyst was removed by filtration, and the solvent evaporated. The residue was recrystallised from 2-propanol/ether yielding 2.2 g of the title compound; mp 190°–91° C.

Pharmacologic properties

The compounds of formula (I) and their pharmaceutically active acid addition salts have useful pharmacological properties. They are useful in treating mental disorders and/or aggression in man and also in treating aggression in animals such as swine, horses and cattle. They are also capable of relieving pain and thus are suitable as analgetics. They have no or very few autonomical side effects and a very low degree of heart toxicity. They also have a very low degree of general toxicity.

Said compounds of formula (I) have a therapeutic activity in the central nervous system having a pharmacological mode of action different from clinically used neuroleptic, antidepressants and anxiolytic agents.

The adverse effects, in particular irreversible tardive dyskinesia induced by (long-term) neuroleptic treatment, constitute a serious drawback to antipsychotic pharmacotherapy. Alternatives to the drugs currently used in psychiatric medicine have therefore been urgently sought for. There is also a need for better antidepressants with fewer and less severe side effects, especially the cardiotoxic ones. The therapeutic effectiveness of known antidepressants is still far from ideal, meaning that in most cases electroconvulsive treatment is more effective than any antidepressant drug in use today.

In contrast to the prior art compounds of formula (A) and (B), which reduce d-amphetamine-induced stereotypy at about the same dose levels as they cause other neuropharmacological effects, the compounds of the present invention quite unexpectedly have been found not to reduce d-amphetamine-induced stereotypy. The ability to reduce d-amphetamine-induced stereotypy is a characteristic action of almost all drugs which block central dopamine receptors and has been commonly used as an index of potential antipsychotic action in man. However, a disruption of striatal dopamine function is thought to underlie this behavioural change. The extrapyramidal side-effects of neuroleptics have been shown to be associated with disturbed dopamine neurotransmission in striatum. Hence, this would indicate that this behavioural model is more likely to predict the potential side-effects, rather than antipsychotic actions of a new compound. In this respect, although enjoying a considerable success in the treatment of schizophrenia, neuroleptic agents have gained a notoriety for the disabling motor side effects which can accompany their use.

The compounds of formula (I), in contrast to known neuroleptics do not inhibit d-amphetamine induced stereotypies or cause motor impairments such as catalepsy. On the other hand they antagonise d-amphetamine induced locomotor hyperactivity. They decrease exploratory behaviour and also demonstrate an action on conditioned avoidance response (CAR), one of the most frequently used screening tests in the development of antipsychotic drugs, qualitatively similar to that reported for classical neuroleptic drugs.

The compounds of formula (I) are potent antiaggressive agents. Like clinically used neuroleptics, antidepressants and anxiolytics they inhibit aggressive behaviour amongst male mice made aggressive by isolation. The compounds like antidepressant drugs in current therapeutic use have been demonstrated to be potent also in antagonizing the muricidal behaviour of rats, a test model well established in screening for clinically effective antidepressants.

The compounds of formula (I) are active in the writhing test. The writhing test is a classical pain test in which the antinociceptive effects of many classical analgesics have been demonstrated. Clearly, when activity is observed in this test during screening of new compounds, they are presumed to be worthy of further attention as potential analgesics. In the writhing test, like morphine, a drug most widely used in human beings for analgesic purposes, the compounds of the present invention display a very marked antinociceptive effect. Importantly, the compounds of the present invention have been demonstrated, in contrast to morphine, not to create physical dependence.

The potency of the compounds in formula (I) and their pharmaceutically active acid addition salts as agents for treatment of mental disorders and pain is clearly evidenced by the results obtained in the following tests.

Test 1: Isolation induced aggressive behaviour test

Male mice subjected to prolonged isolation develop aggressive behaviour against each other when paired (Yen, C. Y. et al., Arch. Int. Pharmacodyn. 123, 179, (1959): Valzelli, L., Adv. Pharmacol. 5, 79 (1967)). All clinically used neuroleptics and antidepressants studied in this test inhibit this aggressive behaviour although their activity may differ. Also anxiolytic drugs, e.g. diazepam, are active on this kind of aggressive behaviour. The clinical correlation of this test indicates tranquillizing and anxiolytic activities as well as antiaggressive properties as such (Duncan, R. L. et al., J Med. Chem. 13, 1 (1970)).

This type of aggression is interesting because it is known that this kind of emotional behaviour might be located in limbic structures in the brain (MacLean, P.D., Psychosom. Med. 11, 338 (1949)).

Every week male NMRI mice, weighing 20–22 g, were isolated in Makrolon cages for three weeks with diet and water ad libitum. A piece of cardboard was placed between the cages to prevent visual contact.

To test aggressiveness the mice were paired in a neutral area, a beaker (14 cm high and diameter 14 cm). A pair is considered aggressive if both the animals show clear signs of fighting within 5 minutes. This fighting is characterized by biting and vocalization. As soon as fighting is seen, the mice are separated and brought to their home cage (every second mouse is marked.) If only one of two mice exhibit aggressive behaviour the aggressive one is paired with another to make a well matched, aggressive pair. Animals showing no aggression are discarded. The frequency of paired mice exhibiting fighting varies from 50–100 per cent depending on the time of the year. The test substance is administered s.c. (0.2–0.4 ml/20 g). The mice are paired 0.5 hour after the injection for trials of 5 minutes duration.

The $ED_{50}$-value (mg/kg) reported is the dose inhibiting aggressive behaviour among 50 per cent of the pairs 0.5 hour after drug administration.

Test 2: Conditioned avoidance response (CAR)

The effect of the test compounds on CAR was evaluated in a shuttle box, manufactured by Ugo Basile, Italy. The female rats, weighing 150 g, were trained to avoid an electric shock (unconditioned stimulus—US) by escaping from one compartment to the other when the light from a 15W lamp is switched on (conditioned stimulus—CS). When they responded to the CS, a conditioned response (CR) was considered to have been elicited. Rats showing a stable CR of more than 80% after a three weeks' training program were used in the experiments. Groups of six rats were subcutaneously administered with various doses of the test compounds. 1½ hours after the administration each rat was placed in the experimental box and the effect on CR was evaluated. $ED_{50}$-values refer to the dose inhibiting CR in 50% of the animals. The mechanisms regulating conditioned responses are very complex. Both catecholaminergic and hormonal factors are of importance.

Test 3: Writhing test

The writhing test is a frequently used test of analgetic properties (Witkin, L. B. et al., J. Pharmacol. Exp. Ther. 133, 400 (1961)). If acetic acid (0.5%, 15 ml/kg) is injected intraperitoneally in mice (NMRI) they will without exception develop a writhing behaviour characterized by stretching their hind legs. The drugs to be tested were administered subcutaneously to 6 female mice at each dose 20 minutes before the injection of the acetic acid. After 10 minutes the behaviour of the mice was studied in 5 minutes. The $ED_{50}$-value is the dose blocking the writhing behaviour in 50% of the animals during the 5 minutes study period.

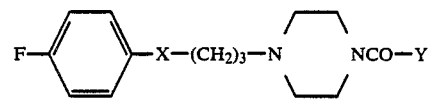

TABLE 1

| Isolation induced aggressive behaviour test | | | |
|---|---|---|---|
| Compound | X | Y | $ED_{50}$, mg/kg, s.c. |
| 1:15 | $CH_2$ | NHEt | 3.5 |
| 1:3 | CO | NHEt | 1.7 |
| Chlorpromazine[a] | | | 1.4 |
| Thioridazine[b] | | | 5 |

TABLE 1-continued

| Isolation induced aggressive behaviour test | | | |
|---|---|---|---|
| Compound | X | Y | $ED_{50}$, mg/kg, s.c. |
| Amitriptyline[c] | | | 5 |
| Diazepam[d] | | | 6.7 |

[a]The Merck Index, 10th Ed., 2163
[b]The Merck Index, 10th Ed., 9202
[c]The Merck Index, 10th Ed., 496
[d]The Merck Index, 10th Ed., 2967

TABLE 2

| Conditioned avoidance response | | | |
|---|---|---|---|
| Compound | X | Y | $ED_{50}$, mg/kg, s.c. |
| 1:15 | $CH_2$ | NHEt | 7.9 |
| 1:3 | CO | NHEt | 12 |
| Chlorpromazine[a] | | | 3.5 |
| Thioridazine[b] | | | 41 |

[a]The Merck Index, 10th Ed., 2163
[b]The Merck Index, 10th Ed., 9202

TABLE 3

| Writhing test | | | |
|---|---|---|---|
| Compound | X | Y | $ED_{50}$, mg/kg, s.c. |
| 1:15 | $CH_2$ | NHEt | 3.7 |
| 1:3 | CO | NHEt | 1.9 |
| Morphine[a] | | | 1.6 |

[a]The Merck Index, 10th Ed., 6129

The compounds listed in table 1, 2 and 3 are not given for the purpose of limiting the invention thereto, but only to exemplify the useful pharmacological activities of compounds within the scope of formula (I).

The compounds of formula (I) and their pharmaceutically active acid addition salts are useful in the control of mental disorders in humans. For example they may be useful for the prophylaxis and/or treatment of schizophrenia, mania or senile, involutional or organic psychoses as well as depressive psychosis.

The new compounds may also be used in the prophylaxis and treatment of aggressive behaviour, which may be associated with mentally retarded and/or behaviourally disturbed patients and other forms of aggression of either known or unknown etiology.

The new compounds are very useful in the treatment of aggressive behaviour in animals, especially in pigs, and also in promoting the development of a natural hierarchy in groups of animals without bursts of aggression and in calming of anxious and stressed animals. Effective quantities of any of the foregoing pharmacologically active compounds of formula (I) may be administered to a human being or an animal for therapeutic purposes according to usual routes of administration and in usual forms, such as orally in solutions, emulsions, suspensions, pils, tablets and capsules, in pharmaceutically acceptable carriers and parenterally in the form of sterile solutions. For the parenteral administration of the actile substance the carrier of excipient may be a sterile, parenterally acceptable liquid, e.g. water, or a parenterally acceptable oil, e.g. arachidic oil.

Although very small quantities of the active materials of the present invention are effective when minor therapy is involved or in the cases of administration to subjects having a relatively low body weight, unit dosages are usually from 2 milligrams upwards, preferably 25, 50 or 100 milligrams or even higher depending on the condition to be treated and the age and weight of the patients as well as the response to the medication.

The unit dose may be from 0.1 to 200 milligrams, preferably from 10 to 50 milligrams. Daily dosages should preferably range from 10 milligrams to 400 milligrams. The exact individiual dosages as well as daily dosages will, of course, be determined according to standard medical principles under the direction of a physician or veterinarian.

The following formulations are representative for all of the pharmacologically active compounds of this invention. Example of a suitable capsule formulation:

| | Per capsule, mg |
|---|---|
| Active ingredient, as salt | 10 |
| Lactose | 250 |
| Starch | 120 |
| Magnesium stearate | 5 |
| Total | 385 |

In case of higher amounts of active ingredient, the amount of lactose used may be reduced.

Example of a suitable tablet formulution:

| | Per tablet, mg |
|---|---|
| Active ingredient, as salt | 10 |
| Potato starch | 90 |
| Colloidal silica | 10 |
| Talc | 20 |
| Magnesium stearate | 2 |
| 5% Aqueous solution of gelatin | 25 |
| Total | 157 |

Solutions for parenteral applications by injection can be prepared in an aqueous solution of a water-soluble pharmaceutically acceptable salt of the active substance preferably in a concentration of from about 0.5% to about 5% by weight. These solutions may also contain stabilizing agents and/or buffering agents and may conveniently be provided in various dosage unit ampoules.

The pharmaceutical preparations may also contain therapeutically useful substances other than the pharmacologically active compounds of formula (I).

We claim:

1. 1-piperazinecarboxamide derivatives which have the general formula (I)

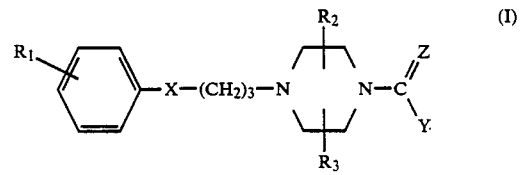

and the pharmaceutically acceptable acid addition salts thereof;
wherein $R_1$ is a member selected from hydrogen, halogen or trifluoromethyl;
  wherein X is selected from:
    >CO (Ia)
    >CHOH (Ib) >$CHOR_8$ (Ib') >$CHOCOR_8$ (Ib")
    >CH2 (Ic)
    >C=$CR_6R_7$ (Id)
    >CH - $CHR_6R_7$ (Ie)

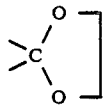
(If)

wherein $R_2$ and $R_3$ are the same or different and selected from hydrogen or lower alkyl;

wherein Z is either oxygen or sulfur; wherein Y is $-NR_4R_5$, where $R_4$ and $R_5$ are the same or different and selected from hydrogen, alkyl, alkenyl, cycloalkyl, aryl, aryl-(lower alkyl), or $R_4$ and $R_5$ may together with the N-atom form a 5- or 6- or 7-membered saturated ring, where one of the carbon atoms may be exchanged for O, $NR_8$ or $NCOR_8$;

wherein $R_6$ and $R_7$ are the same or different and selected from hydrogen or lower alkyl;

wherein $R_8$ is lower alkyl or lower alkenyl;
and when used in the foregoing definitions the term "lower alkyl" is meant to include straight and branched hydrocarbon radicals having from 1 to 4 carbon atoms; the term "lower alkenyl" is meant to include straight and branched alkenyl radicals having from 2 to 4 carbon atoms; the term "alkyl" is meant to include straight and branched hydrocarbon radicals having from 1 to 10 carbon atoms; the term "alkenyl" is meant to include straight and branched alkenyl radicals having from 2 to 10 carbon atoms; the term "cycloalkyl" is meant to include cyclic hydrocarbon radicals having from 3 to 8 carbon atoms; the term "aryl" is meant to include phenyl and substituted phenyl, wherein said substituted phenyl has from 1 to 3 substituents, each independently selected from the group consisting of halogen, methyl, methoxy, trifluoromethyl and $NR_2R_3$; and the term "halogen" is meant to include fluoro, chloro and bromo;

with the provisio that when X is >CO, then $R_4$ is hydrogen and $R_5$ is different from hydrogen.

2. 1-piperazinecarboxamide derivatives according to claim 1 wherein X is >CO (Ia).

3. Pharmaceutical composition characterized by containing as an active ingredient an 1-piperazinecarboxamide derivative according to claim 1 together with a pharmaceutical acceptable carrier.

4. Derivatives according to claim 1 wherein X is selected from the group consisting of $CH_2$; $C=R_6R_7$; and $CH-CHR_6R_7$.

5. Derivatives according to claim 4 wherein $R_2$ and $R_3$ are hydrogen.

6. Derivatives according to claim 1 wherein X is selected from the group consisting of CHH, $CHOR_8$, and $CHOCOR_8$.

7. Derivatives according to claim 6 wherein $R_2$ and $R_3$ are hydrogen.

8. A method for treating mental disorders comprising administering to a patient having a mental disorder an effective amount of a compound according to formula I of claim 1 in a pharmaceutically acceptable carrier.

9. A method for providing analgesia to a patient in need of analgesia comprising administering to said patient an effective amount of a compound according to formula I of claim 1 in a pharmaceutically acceptable carrier.

10. A method for treating aggression in an animal comprising administering to said aggressive animal an effective amount of a compound according to formula I of claim 1 in a pharmaceutically acceptable carrier.

11. A method for calming an anxious and stressed animal comprising administering to said animal an effective amount of a compound according to formula I of claim 1 in a pharmaceutically effective carrier.

12. 1-piperazine carboxamide according to claim 1 which is 4-4[4-(p-fluorophenyl)-4-oxobutyl]N-cyclohexyl-1-piperazine carboxamide.

* * * * *